United States Patent
Roewer et al.

(10) Patent No.: US 9,925,274 B2
(45) Date of Patent: *Mar. 27, 2018

(54) DELPHINIDIN COMPLEX AS AN ANTIPHLOGISTIC OR IMMUNOSUPPRESSIVE ACTIVE INGREDIENT

(71) Applicant: Sapiotec GmbH, Wurzburg (DE)

(72) Inventors: Norbert Roewer, Wurzburg (DE); Jens Broscheit, Wurzburg (DE)

(73) Assignee: SAPIOTEC GMBH, Wurzburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/443,166

(22) PCT Filed: Nov. 1, 2013

(86) PCT No.: PCT/EP2013/072856
§ 371 (c)(1),
(2) Date: May 15, 2015

(87) PCT Pub. No.: WO2014/075935
PCT Pub. Date: May 22, 2014

(65) Prior Publication Data
US 2015/0306247 A1    Oct. 29, 2015

(30) Foreign Application Priority Data
Nov. 15, 2012 (EP) ..................... 12192717

(51) Int. Cl.
| A61K 31/7048 | (2006.01) |
| A61K 47/40 | (2006.01) |
| A61K 47/48 | (2006.01) |
| A61K 9/08 | (2006.01) |
| A61K 9/14 | (2006.01) |
| A61K 31/724 | (2006.01) |
| A61K 45/06 | (2006.01) |
| A61K 31/353 | (2006.01) |
| A61K 31/352 | (2006.01) |
| A61K 47/69 | (2017.01) |

(52) U.S. Cl.
CPC .......... *A61K 47/48969* (2013.01); *A61K 9/08* (2013.01); *A61K 9/146* (2013.01); *A61K 31/352* (2013.01); *A61K 31/353* (2013.01); *A61K 31/724* (2013.01); *A61K 45/06* (2013.01); *A61K 47/40* (2013.01); *A61K 47/6951* (2017.08)

(58) Field of Classification Search
None
See application file for complete search history.

(56) References Cited

U.S. PATENT DOCUMENTS

| 4,826,963 A | 5/1989 | Stadler nee Szoke et al. |
| 5,134,127 A | 7/1992 | Stella et al. |
| 6,576,261 B1 | 6/2003 | Pitha |
| 6,699,849 B1 | 3/2004 | Loftsson et al. |
| 7,034,013 B2 | 4/2006 | Thompson et al. |
| 8,980,882 B2 | 3/2015 | Roewer et al. |
| 9,006,215 B2 | 4/2015 | Roewer et al. |
| 9,125,953 B2 | 9/2015 | Roewer et al. |
| 2004/0101933 A1 | 5/2004 | Matsumoto et al. |
| 2005/0013880 A1 | 1/2005 | Magnuson et al. |
| 2005/0164986 A1 | 7/2005 | Mosher |
| 2007/0093448 A1 | 4/2007 | Westermann et al. |
| 2007/0232688 A1 | 10/2007 | Orchansky et al. |
| 2009/0270348 A1 | 10/2009 | Antle |
| 2011/0015145 A1 | 1/2011 | Bodor |
| 2011/0028386 A1 | 2/2011 | Hodges et al. |
| 2011/0224168 A1 | 9/2011 | Szente |
| 2012/0083460 A1 | 4/2012 | Emura et al. |
| 2015/0051273 A1 | 2/2015 | Roewer et al. |
| 2015/0087822 A1 | 3/2015 | Roewer et al. |
| 2015/0258202 A1 | 9/2015 | Roewer et al. |
| 2015/0320719 A1 | 11/2015 | Roewer et al. |
| 2015/0328336 A1 | 11/2015 | Roewer et al. |

FOREIGN PATENT DOCUMENTS

| CN | 1672534 | 9/2005 |
| DE | 102010042615 | 4/2012 |
| EP | 0214647 | 3/1987 |
| EP | 0390496 | 10/1990 |
| EP | 1704858 | 9/2006 |
| GB | 2350297 | 11/2000 |
| JP | 59-46228 | 3/1984 |
| JP | 2003-171274 | 6/2003 |
| JP | 2003-522207 | 7/2003 |
| JP | 2004-526730 | 9/2004 |
| JP | 2005-522422 | 7/2005 |
| JP | 2009-167174 | 7/2009 |
| KR | 10-2007-0026284 | 3/2007 |

(Continued)

OTHER PUBLICATIONS

Kanakis et al., DNA Interaction with Naturally Occurring Antioxidant Flavonoids Quercetin, Kaempferol, and Delphinidin, pp. 719-724, published online: May 15, 2012.*
Kumoro et al, Solubility of Delphinidin in Water and Various Organic Solvents between (298.15 and 343.15) K; 2012; J. Chem. Eng. Data; 55: 2603-2606.*
U.S. Appl. No. 14/651,262, filed Jun. 2015, Roewer, US Classification 514/777.*
U.S. Appl. No. 14/389,474, filed Sep. 2014, Roewer, US Classification 514/777.*
U.S. Appl. No. 14/432,654, filed Mar. 2015, Roewer, US Classification 514/777.*
Bertuglia et al., Microvascular Effects of a Natural Flavonoid (IdB 1056) During Ischemia-Reperfusion Injury, Pharmacological Research 1990; 22:52, Abstract.

(Continued)

*Primary Examiner* — Svetlana M Ivanova
(74) *Attorney, Agent, or Firm* — Casimir Jones, S.C.; Mary Ann Brow (57) ABSTRACT

The invention relates to a composition comprising a complex of delphinidin and a sulfoalkyl ether β-cyclodextrin for use as an antiphlogistic and/or immunosuppressive.

19 Claims, 5 Drawing Sheets

(56) References Cited

FOREIGN PATENT DOCUMENTS

| KR | 10-2007-0028640 | * | 3/2007 | ............ A61K 31/352 |
|---|---|---|---|---|
| KR | 10-2007-028640 | | 3/2007 | |
| WO | WO 1996/32135 | | 10/1996 | |
| WO | WO 1997/17977 | | 5/1997 | |
| WO | WO 1999/24073 | | 5/1999 | |
| WO | WO 1999/42211 | | 8/1999 | |
| WO | WO 2001/030391 | | 5/2001 | |
| WO | WO 2002/074200 | | 9/2002 | |
| WO | WO 2003/063824 | | 8/2003 | |
| WO | WO 2003/080079 | | 10/2003 | |
| WO | WO 2006/076387 | | 7/2006 | |
| WO | WO 2008/070490 | | 6/2008 | |
| WO | 2008/126979 | | 10/2008 | |
| WO | WO 2009018326 A2 | * | 2/2009 | ............ A61K 31/352 |
| WO | 2009/134347 | | 11/2009 | |
| WO | 2011/048479 | | 4/2011 | |
| WO | WO 2011/086146 | | 7/2011 | |
| WO | WO 2012/090018 | | 7/2012 | |
| WO | WO 2013/144297 | | 10/2013 | |
| WO | WO 2013/144303 | | 10/2013 | |
| WO | WO 2013/144306 | | 10/2013 | |
| WO | WO 2014/060548 | | 4/2014 | |
| WO | WO 2014/075935 | | 5/2014 | |
| WO | WO 2014/090583 | | 5/2014 | |
| WO | WO 2014/090586 | | 6/2014 | |
| WO | WO 2015/128419 | | 9/2015 | |
| WO | WO 2015/128437 | | 9/2015 | |

OTHER PUBLICATIONS

Scarabelli et al., Targeting STAT1 by myricetin and delphinidin provides efficient protection of the heart from ischemia/reperfusion-induced injury, FEBS Lett. Feb. 4, 2009;583(3):531-41.
Ueda et al., Evaluation of a sulfobutyl ether beta-cyclodextrin as a solubilizing/stabilizing agent for several drugs, Drug Dev Ind Pharm. Sep. 1998;24(9):863-7.
Abdollahzadeh et al., Antibacterial and Antifungal Activities of Punica Granatum Peel Extracts Against Oral Pathogens. Journal of Dentistry, Tehran University of Medical Sciences 2011; 8: 1-6.
Afaq et al., Delphinidin, an anthocyanidin in pigmented fruits and vegetables, protects human HaCaT keratinocytes and mouse skin against UVB-mediated oxidative stress and apoptosis. J Invest Dermatol. Jan. 2007;127(1):222-32.
Armstrong et al., Separation of drug stereoisomers by the formation of beta-cyclodextrin inclusion complexes. Science. May 30, 1986;232(4754):1132-5.
ATCC product sheet for A-375 [A375] (ATCC CRL-1619), retrieved Nov. 16, 2015, 3 pages.
Biofiles: Nutrition Research. Sigma-Aldrich. 2007;2:1-28.
Biolink synthetic anthocyanin molecules becomes cancer fighters, www.biolink.no/biolink/cancer-articles95-6.html, May 22, 2009, 4 pages.
Braga et al., Inclusion of molybdenocene dichloride (Cp2MoCl2) in 2-hydroxypropyl- and trimethyl-beta-cyclodextrin: Structural and biological properties. Journal of Organometallic Chemistry, 2005; 690:2905-2912.
Brewster et al., Cyclodextrins as pharmaceutical solubilizers. Adv Drug Deliv Rev. Jul. 30, 2007;59(7):645-66.
Bruggen, Detection of phenotypic differences on human malignant melanoma lines and their variant sublines with monoclonal antibodies, Cancer Immunol Immunother, 1983, 15:200-205.
Burdulis et al., "Comparative Study of Anthocyanin Composition, Antimicrobial and Antioxidant Activity in Bilberry (*Vaccinium myrtillus* L.) and Blueberry (*Vaccinium corymbosum* L.) Fruits." Acta Poloniae Pharmaceutica 2009; 66:399-408.
Cyclobond Handbook, A Guide to Using Cyclodextrin Bonded Phases for Chiral LC Seperations, 6th ed., 2002, Advanced Seperation Technologies, Inc., pp. 1-58.
Eftink et al., Calorimetric studies of p-nitrophenol binding to alpha- and beta-cyclodextrin. Bioorganic Chemistry. 1981;10:388-398.
Hornle et al., Caspase-3 cleaves XIAP in a positive feedback loop to sensitize melanoma cells to TRAIL-induced apoptosis. Oncogene. Feb. 3, 2011;30(5):575-87.
Hutajalu et al., "Identification of Phenol and Delphinidine in the Telangs flower (*Clitoria ternatea* L.) and its Effectivity to *Staphylococcus aureus* as Eyes Bacteria Disease." Journal of Agro-Based Industry 2008; 25: 35-44.
Ibrahium, Efficiency of Pomegranate Peel Extract as Antimicrobial, Antioxidant and Protective Agents. World Journal of Agricultural Sciences 2010; 6: 338-344.
Immel, Ph.D. Thesis, Darmstadt University of Technology, 1995. Computer Simulation of Chemical and Biological Properties of Saccharides: Sucrose, Fructose, Cyclodextrins, and Starch; Chapter 7. "Some Reflections on the Multitude of Cyclodextrin Isomers: Astronomic Numbers as a Justification for Computational Studies prior to Synthesis", 9 pages.
Jara et al., The interaction of solvtochromic pyridiniophenolates with cyclodextrins. Tetrahedron. 2006;62:7817-7823.
Kamei et al., "Suppression of tumor cell growth by anthocyanins in vitro." Cancer Invest 1995; 13: 590-594.
Kumoro et al., Solubility of Delphinidin in Water and Various Organic Solvents between (298.15 and 343.15)K. J Chem Eng Data. 2012;55:2603-2606.
Lecis et al., Novel SMAC-mimetics synergistically stimulate melanoma cell death in combination with TRAIL and Bortezomib. Br J Cancer. Jun. 8, 2010;102(12):1707-16.
Naber, *Staphylococcus aureus* Bacteremia: Epidemiology, Pathophysiology, and Management Strategies. Clin Infect Dis. 2009;48(Suppl 4):S231-S237.
Riccardi et al., Analysis of apoptosis by propidium iodide staining and flow cytometry. Nat. Protoc., 2006, 1:1458-1461.
Serafino et al., Differentiation of human melanoma cells induced by cyanidin-3-O-beta-glucopyranoside, FASEB J. Dec. 2004;18(15):1940-2.
Stella et al., Cyclodextrins: their future in drug formulation and delivery. Pharm Res. May 1997;14(5):556-67.
Ukoka et al., Tannins and other phytochemical of the Samanaea saman pods and their antimicrobial activities, African Journal of Pure and Applied Chemistry 2011; 5: 237-244.
Vierstein et al., Intravenous anasthesia with isoflurane in the rabbit. Pharm Pharmacol Lett, 1994; 3:165-168.
Vierstein et al., Preparation and central action of propofol/hydroxypropyl-beta-cyclodextrin complexes in rabbits. Arzneimittelforschung. Aug. 1993;43(8):818-21.
Wang et al., Anthocyanins and their role in cancer prevention, Cancer Lett. Oct. 8, 2008;269(2):281-90.
English translation of IPRP for International Patent Application PCT/EP2011/050428, dated Aug. 16, 2012, 8 pages.
International Search Report for PCT/EP2013/056707, dated Mar. 28, 2013, 13 pages. With Translation.
International Search Report for PCT/EP2013/056725 dated Apr. 7, 2013, 17 pages. With Translation.
International Search Report for PCT/EP2013/071779 dated Dec. 10, 2013, 12 pages. With Translation.
International Search Report for PCT/EP2015/054023 dated Mar. 23, 2015, 10 pages. With Translation.
International Search Report for PCT/EP2015/054084 dated May 4, 2015, 17 pages. With Translation.

* cited by examiner

DELPHINIDIN COMPLEX AS AN ANTIPHLOGISTIC OR IMMUNOSUPPRESSIVE ACTIVE INGREDIENT

This application is a § 371US National Entry of International Application No. PCT/EP2013/072856, filed Nov. 1, 2013, which claims the benefit of European Application No. 12192717.2, filed Nov. 15, 2012.

The invention relates to the use of compositions comprising a complex composed of delphinidin and a sulfoalkyl ether β-cyclodextrin and/or delphinidin or the salts thereof as an anti-inflammatory and/or an immunosuppressant.

Responses of the immune system are mediated by the components of the innate and acquired immune system. The innately nonspecific immune system encompasses all responses to antigens and exogenous stimuli (bacteria, viruses, fungi, etc.) which start from macrophages, monocytes and granulocytes, and also humoral defense mechanisms including interferon, defensins and acute phase proteins. The acquired or adaptive immune system encompasses all specific defense responses which start from lymphocytes, more particularly from B lymphocytes (B cells) and T lymphocytes (T cells). Under certain conditions, the responses of the immune system itself can be the cause of diseases or disease-relevant states. Such diseases or states are, for example, acute and chronic inflammations, sepsis, autoimmune diseases or rejections following an organ, cell or tissue transplant. In the event of these and other states, in which there is an inadequate or undesired immune response, immunosuppression by means of anti-inflammatories or immunosuppressants is necessary from a clinical point of view.

An anti-inflammatory or antiphlogistic substance is a substance capable of reducing or inhibiting an inflammation or one of its manifestations in part or in full, at once or after a delay. An antiphlogistic substance can either be directed to soluble mediators such as cytokines or modulate the expression of certain cellular surface receptors involved in an inflammatory response, such as, for example, MHC class II molecules. An immunosuppressant substance is a substance which acts on the immune system, resulting in an immediate or delayed reduction in the activity of the immunological system. An immunosuppressant substance is used when there is an excessive immune response, for example against endogenous molecules or tissue or against transplanted tissue, for example autoimmune diseases, type I diabetes, multiple sclerosis or rheumatoid arthritis. Anti-inflammatories currently used are, for example, acetylsalicylic acid, diclofenac, indomethacin or glucocorticoids. From the group of immunosuppressants, cell division inhibitors (azathioprine), calcineurin inhibitors (tacrolimus, cyclosporine, pimecrolimus) and hydrocortisone are used.

In daily clinical practice, hydrocortisone is used for inflammation inhibition and immunosuppression and is for example applied locally in the rectum to alleviate inflammatory symptoms in the case of inflammatory bowel disease, such as ulcerative colitis, Crohn's disease, or in the case of other inflammations of the lower part of the intestine, such as proctosigmoiditis. Likewise known is the use of hydrocortisone in creams and ointments for application to the skin in the case of inflammatory or allergic skin diseases such as eczemas, neurodermitis, psoriasis, sunburn, skin infections and insect bites, in order to bring about an alleviation of complaints such as itching or inflammations.

Whereas the short-term administration of even high hydrocortisone doses is generally still well tolerated by the body, undesired adverse effects do occur in the case of longer treatment and, more particularly, in the case of internal administration of the active ingredient. The internal administration of the active ingredient has two substantial adverse effects. Firstly, hydrocortisone promotes the retention of water from the urine into the blood. This increases the amount of blood; the pressure in the blood vessels increases and hence the blood pressure. By this means, it is also possible that high blood pressure occurs long-term. Secondly, hydrocortisone can trigger cardiac arrhythmias. Hydrocortisone increases the excretion of potassium with urine. This can lead to a potassium deficiency which promotes cardiac arrhythmias. Therefore, such preparations are typically applied in clinical practice only from the age of six and for no longer than two weeks.

It is an object of the present invention to provide an effective anti-inflammatory and/or immunosuppressant as an alternative or supplement to anti-inflammatories or immunosuppressants known from the prior art, such as hydrocortisone.

This object is achieved by the compositions and uses claimed in the independent claims, with advantageous embodiments of the invention being disclosed in the dependent claims. The fact that this object is actually achieved is evidenced by the in vitro and in vivo experimental results relating to the anti-inflammatory and antiphlogistic effect of delphinidin and delphinidin/sulfoethyl ether β-cyclodextrin in the examples 6-11 according to the invention.

Firstly, some terms used in the context of the invention will be explained.

The complex according to the invention or the composition according to the invention are used to treat a subject or individual suffering from an indication and/or requiring a prophylactic treatment, which is preferably selected from the group consisting of inflammatory states or inflammatory diseases, diseases associated with inflammatory tissue changes, rejections following a transplant and autoimmune diseases.

"Inflammatory states or inflammatory diseases" in the context of the present invention encompass indication such as, for example, rheumatoid arthritis, chronic polyarthritis, juvenile idiopathic arthritis, spondylitis, osteoarthritis, sepsis, septic shock, cerebral malaria, a chronic inflammatory lung disease, silicosis, sarcoidosis, reperfusion syndrome, neurodegenerative or neuroinflammatory diseases, such as Crohn's disease, multiple sclerosis and Parkinson's disease, ulcerative colitis, fever in the case of infections and also depressions which are likewise caused by inflammatory tissue responses [Pace et al. (2006), Increased stress-induced inflammatory responses in male patients with major depression and increased early life stress. Am. J. Psychiatry. 163(9): 1630-3].

Inflammatory responses can likewise be observed in the course of a reduced myocardial and/or cerebral blood supply (ischemia), more particularly after restored blood supply (reperfusion), in which the necrotic swelling of the cells leads to the break-up of the cell membrane and associated release of the constituents of the cytoplasm, which cause an inflammatory response. The complex according to the invention or the composition according to the invention thus also has, according to the invention, a use which can be considered to be that of tissue and/or organ protection in the context of cerebral and/or myocardial ischemia and correlate with the clinical symptoms of stroke and of myocardial infarction. In a preferred embodiment of the invention, the use of the complex according to the invention or the composition according to the invention by the affected tissue or organ averts or softens additional damage (reperfusion paradox), as evidenced in the investigations of exemplary embodiment 10.

Atherosclerosis-associated diseases, including in particular stroke, coronary heart disease (CHD) and peripheral artery occlusive disease, affect people in industrial countries to a considerable extent. Currently, over 7 million people die each year as the result of ischemic heart diseases. CHD causes an inadequate blood supply and associated insufficient supply of oxygen to the cardiac muscle (myocardial ischemia), and the consequence of this is that myocardial infarction and cardiac death may occur. CHD is divided into 6 progressive forms: stable angina pectoris, acute coronary syndrome (unstable angina pectoris and acute myocardial infarction), sudden cardiac death, chronic heart failure, cardiac arrhythmias and also silent myocardial ischemia. With advancing myocardial ischemia, cell death of the cardiocytes ensues owing to "random" (necrosis) and "programmed" (apoptosis) cell death, with the necrotic swelling of the cells leading to the break-up of the cell membranes with release of the cytoplasmic constituents responsible for the inflammatory response.

"Diseases associated with inflammatory tissue changes" include indications such as from the group consisting of Alzheimer's disease, Parkinson's disease and cancer.

The term "subject" encompasses living animals and humans.

The term "composition comprising a complex composed of delphinidin and a sulfoalkyl ether β-cyclodextrin and/or delphinidin or the salts thereof" includes the composition as a monopreparation, i.e., without any further therapeutically active components. Alternatively, the composition can comprise at least one further therapeutically active substance. Said further therapeutically effective substance is preferably selected from the group of the anti-inflammatories, of the antibodies against inflammatory cytokines, of the soluble receptors of inflammatory cytokines or of the immunosuppressants and particularly preferably selected from the group consisting of acetylsalicylic acid, diclofenac, indomethacin, cyclosporine, azathioprine, bortezomib, melphalan, prednisone, vincristine, carmustine, cyclophosphamide, dexamethasone, thalidomide, doxorubicin, cisplatin, etoposide and cytarabine.

The present invention also provides methods for treating a subject suffering from an inflammatory state or an inflammatory disease, from a disease associated with inflammatory tissue changes, a rejection following a transplant or an autoimmune disease, with a therapeutically effective amount of the composition according to the invention being administered to the subject. As already mentioned, the composition according to the invention can be administered alone or in combination with at least one other therapeutic agent. The composition according to the invention can be administered simultaneously with the other therapeutic agent, which can be a constituent of the same composition or is provided in another composition. Alternatively, the composition according to the invention can be administered before or after the administration of the other therapeutic agent. The composition according to the invention can be administered via the same administration route as the other therapeutic agent or via another administration route.

In the context of the present invention, the term "treatment" means attaining the following results in full or in part: total or partial reduction of the symptoms; improvement of at least one of the clinical symptoms or disease-associated indicators; delaying, suppressing or protecting against the progression of the disease; or totally or partly delaying, suppressing or protecting against the breakout or emergence of the disease. The subject to be treated is a person or animal, preferably a mammal. The veterinary medical treatment encompasses not only the treatment of livestock or wild animals (e.g., sheep, cats, horses, cows, pigs), but also laboratory animals (e.g., rats, mice, guinea pigs, apes).

The composition according to the invention is preferably provided and administered as a pharmaceutical composition. The term "pharmaceutical composition" encompasses one or more active ingredients and one or more inert ingredients acting as carrier for the active ingredient(s). The pharmaceutical compositions make it possible to administer the complex according to the invention or the composition according to the invention orally, rectally, parenterally, including intraperitoneally, percutaneously, subcutaneously, intramuscularly, intravenously, ophthalmically, pulmonally or nasally. A parenteral form of administration can, for example, be a tablet, capsule, solution, suspension or dispersion. An ophthalmic, pulmonal or nasal form of administration can, for example, be an aerosol, solution, cream, paste, lotion, gel, ointment, suspension or dispersion. Corresponding techniques for formulation and administration are known from the prior art; see, for example, "Remington's Pharmaceutical Sciences" (Mack Publishing Co., Easton Pa.). For example, the compositions according to the invention can be administered to a target intravenously by means of a pharmaceutically acceptable carrier (e.g., physiological salt solution). In the case of injection, one option is formulation in an aqueous solution, preferably in physiologically acceptable buffers (e.g., Hanks' solution, Ringer's solution or physiologically buffered saline solution). In the case of parenteral administration, including intravenous, subcutaneous, intramuscular and intraperitoneal administration, an aqueous or oily solution or a solids formulation is likewise a possibility. The proportion of the active active ingredient in the pharmaceutical composition can vary and is typically between 2 and 60% by weight of the administration unit. The proportion of active ingredient is appropriately selected such that an effective dose is attained. In a preferred embodiment of the invention, the delphinidin or the salts thereof and/or the complex composed of delphinidin and the sulfoalkyl ether β-cyclodextrin is used in a pharmaceutical preparation for the controlled and/or delayed release of the delphinidin.

"Salt" or "pharmaceutically acceptable salt" means any pharmaceutically acceptable salt of a compound of present invention, which salt can release the pharmaceutically effective active ingredient or the active metabolite thereof after administration. Salts of the compositions and complexes of the present invention can be derived from inorganic or organic acids and bases.

The anthocyanidin delphinidin can be used in "pure form" or "purified", meaning that undesired components have been removed.

"Anthocyanidins" have the basic structure reproduced below.

The substituents in this formula are selected from the group consisting of hydrogen, hydroxyl group and methoxy group.

Cyclodextrins which can be complexed according to the invention with the anthocyanidin delphinidin are cyclic oligosaccharides composed of glucose molecules linked by α-1,4-glycosidic bonds. β-Cyclodextrin has seven glucose units. In the case of a sulfoalkyl ether β-cyclodextrin, hydroxyl groups of the glucose unit are etherified in a sulfoalkyl alcohol. According to the invention, generally only some of the 21 hydroxyl groups of a β-cyclodextrin are etherified. The production of sulfoalkyl ether cyclodextrins is familiar to a person skilled in the art and described in, for example, U.S. Pat. No. 5,134,127 or WO 2009/134347 A2.

Sulfoalkyl ether groups are used in the case of cyclodextrins in the prior art to increase the hydrophilicity or water solubility. Sulfoalkyl ether groups contribute to a particular extent to increasing the stability of the complex composed of anthocyanidins and appropriately substituted β-cyclodextrin, thus substantially improving the storage stability and formulability of the especially oxidation-sensitive anthocyanidins. The complex according to the invention can be formulated as a storage-stable aqueous solution or solid, as will be shown in more detail below. Particular preference according to the invention is given to the complexation of the active ingredient delphindin with a sulfoethyl ether β-cyclodextrin, and this, surprisingly, increases the solubility and stability of the active ingredient. An attempt to explain this, without restricting the scope of protection, is that the negatively charged sulfoethyl units interact electrostatically with the positively charged anthocyanidin delphinidin and, among the alkyl groups, the ethyl group has the optimal length to allow an appropriate interaction from a sterical point of view. It should be noted at this point that it is not possible to make a generally valid statement that any desired active ingredient, for example delphinidin, in a complex with a sulfoalkyl ether β-cyclodextrin leads to an improvement in the solubility and stability. By way of example, reference should be made at this point to table 1 in Ueda et al., "Evaluation of a Sulfobutyl Ether β-Cyclodextrin as a Solubilizing/Stabilizing Agent for Several Drugs", Drug Development and Industrial Pharmacy, 24(9), 863-867 (1998), in which the solubilities of various active ingredients alone, in a complex with sulfobutyl ether β-cyclodextrin and in a complex with β-cyclodextrin are contrasted. From the solubility values shown therein (SBE7-β-CD vs. β-CD), it can be seen that exactly the opposite is the case for a third of the investigated active ingredients in a complex with sulfobutyl ether β-cyclodextrin, i.e., the complex composed of active ingredient and sulfobutyl ether β-cyclodextrin results in a significantly lower solubility compared to the complex with β-cyclodextrin.

Preferably, the degree of substitution of the cyclodextrin with sulfoalkyl ether groups is from 3 to 8, more preferably from 4 to 8, more preferably from 5 to 8, more preferably from 6 to 7. Likewise usable are sulfobutyl ether β-cyclodextrins having a similar degree of substitution; for instance, appropriate cyclodextrins having a medium degree of substitution of from 6 to 7 are, for example, described in the aforementioned WO 2009/134347 A2 and commercially available under the trade name Captisol®. Likewise usable are appropriate cyclodextrins having a degree of substitution of from 4 to 5, for example 4.2.

The anthocyanidin used according to the invention in pure, salt or complexed form is delphinidin. The chemical structure corresponds to the above-reproduced formula having the following substitution pattern

| | $R^{3'}$ | $R^{4'}$ | $R^{5'}$ | $R^3$ | $R^5$ | $R^6$ | $R^7$ |
|---|---|---|---|---|---|---|---|
| Delphinidin | —OH | —OH | —OH | —OH | —OH | —H | —OH |

The invention further provides an aqueous solution of the composition according to the invention for use as a medicament according to the claims.

The production of the complex according to the invention and of an appropriately aqueous solution comprises the following steps:
a) producing an aqueous solution of the sulfoalkyl ether β-cyclodextrin,
b) adding and mixing the anthocyanidin delphinidin to produce the complex.

In step a), preference is given to producing an aqueous solution containing from 5 to 10% by weight of the cyclodextrin used. In the context of the invention, particular preference is given to adjusting the pH of the aqueous solution during or after, though preferably before, the addition of the delphinidin to a pH of 7 or less, preferably 6 or less, more preferably 5 or less, more preferably from 4 to 5. It has been found that said pH makes it possible to set a relatively high concentration of the complex in aqueous solution.

The concentration of the delphinidin, calculated as chloride, is preferably at least 0.5 mg/ml, more preferably at least 1.0 mg/ml, more preferably at least 1.5 mg/ml, more preferably 2.0 mg/ml. The particularly preferred concentration range of at least 2.0 mg/ml can be set in particular, in the context of a preferred embodiment, in an aqueous solution having a pH between 4 and 5.

As part of the production, the mixing of the constituents of the aqueous solution can be effected by stirring; preferred mixing times are from 2 to 20 h. Preference is given to working in the dark in order to avoid a light-induced oxidation.

The invention further provides a solid for use as a medicament, which solid is obtainable according to the invention by removing the solvent from an above-described aqueous solution according to the invention.

The removal can preferably be effected by freeze-drying (lyophilization). Both the aqueous medicamentous solution according to the invention and the medicamentous solid have a high storage stability.

The invention shall now be described below in detail in the examples with reference to the attached figures, without being restricted thereto.

EXAMPLES

I. Production of a Complex Composed of Delphinidin and Cyclodextrins

1. Materials Used:

The following cyclodextrins are used:

| | |
|---|---|
| α-CD | ID No: CYL-2322 |
| β-CD | ID No: CYL-3190 |
| γ-CD | ID No: CYL-2323 |
| (2-Hydroxypropyl)-β-CD | ID No: L-043/07 |
| Sulfobutyl ether β-CD | ID No: 47K010111 |

Delphinidin chloride was purchased from Extrasynthese.

2. Determination of the Delphinidin Content

The content of delphinidin chloride in the delphinidin-containing compositions was determined by using a reverse-phase HPLC method. This used the following reagents:

Purified water
Methanol for chromatography
Formic acid, p. a.
1 M Hydrochloric acid as volumetric solution.

The column used was a Waters X Bridge™ C18, 35 µl, 150 mm×4.6 mm.

The mobile phases were as follows:
Channel A: water (950 ml), methanol (50 ml), formic acid (10 ml)
Channel B: water (50 ml), methanol (950 ml), formic acid (10 ml)

The following gradient program was used:

| Time [min] | Percent channel B |
|---|---|
| 0 | 0 |
| 5 | 0 |
| 25 | 60 |
| 30 | 100 |

Stop time: 35 min
Posttime: 8 min
Flow rate: 1 ml/min
Injection volume: 20 µl
Column temperature: 30° C.+/−2° C.
UV/Vis detector: 530 µm for the assay, 275 µm for detecting impurities
Integrator: area
Solutions and Sample Preparation:
Dilution solution 1: mixture of 100 ml of methanol and 2.6 ml of M HCl
Dilution solution 2: mixture of 100 ml of 40% methanol and 2.6 ml of 1 M HCl Calibration solution: a delphinidin reference solution was produced by weighing out 10 mg of delphinidin chloride into a 10 ml flask and dissolving it in dilution solution 1. After it was dissolved, it was diluted approximately 10-fold using dilution solution 2 to produce an approximate concentration of 0.1 mg/ml.

The control calibration solution was produced in the same manner. The calibration solutions were immediately analyzed by means of HPLC, since delphinidin chloride is unstable in solution.

Production of the Test Solutions:

To determine the delphinidin content of solids produced according to the invention (with regard to production, see further below), about 50 mg of this composition were weighed out in a 10 ml flask. This was then dissolved in dilution solution 2 and further diluted with the same dilution solution 2 until an approximate delphinidin concentration of 0.1 mg/ml was set.

The determination of the delphinidin content in the samples was calculated with the aid of the Agilent ChemStation software using the calibration with the described external standard.

Example 1

Complexation of Delphinidin with SBE-β-CD

In this example, the complexation of delphinidin by means of various cyclodextrins and the solubility of the complex in aqueous solution are investigated. Neutral aqueous solutions containing 10% by weight of the particular cyclodextrin were produced. In the case of β-CD, a concentration of only 2% by weight was selected because of the insufficient solubility.

5 ml of each of the aqueous cyclodextrin solutions and of pure water were filled into glass flasks. An excess of delphinidin chloride was then added. The required excess amount was 10 mg for the solutions of α-, β- and γ-cyclodextrin and 15 mg for the solutions of HPBCD (2-hydroxypropyl-β-cyclodextrin) and SBE-β-CD.

The suspensions were stirred in the dark at 30° C. for 20 h. This was followed by filtration through a membrane filter having a 0.22 µm pore size.

The attainable solubilities are reproduced in table 1 below.

| Cyclodextrin | Cyclodextrin concentration | Delphinidin chloride |
|---|---|---|
| — | 0 | 0.07 mg/ml |
| α-CD | 10% | 0.14 mg/ml |
| β-CD | 2% | 0.05 mg/ml |
| γ-CD | 10% | 0.21 mg/ml |
| HPBCD | 10% | 0.19 mg/ml |
| SBE-β-CD | 10% | 0.66 mg/ml |

It is apparent that the complexation and the resulting increase in solubility is far better for SBE-β-CD than for the other cyclodextrins.

Example 2

Influence of pH

In this example, the influence of pH on the solubility of a delphinidin/SBE-β-CD in aqueous solution was investigated. In accordance with the instructions of example 1, aqueous solutions of SEB-β-CD were produced, though said solutions were adjusted with 1 M HCl to the acidic pH levels stated in table 2. Delphinidin chloride was then added and further processed in accordance with the instructions of example 1, the only deviation being that the stirring time was limited to 2.5 h. The results are reproduced in table 2 below.

| pH | Delphinidin chloride |
|---|---|
| 6.0 | 0.60 mg/ml |
| 4.8 | 2.12 mg/ml |
| 4.1 | 2.03 mg/ml |

It is apparent that, for pH levels between 4 and 5, the solubility of the complexed delphinidin chloride increases by about a factor of 3 with respect to a neutral pH.

Example 3

Production of a Solid According to the Invention

In this example, a complex according to the invention is formulated as a solid. For the purposes of comparison, a delphinidin/HPBCD complex and a delphinidin/starch formulation are prepared as solids.

Example 3.1

Delphinidin/SBE-β-CD 5 g of SEB-β-CD were dissolved in 40 ml of distilled water to give a clear solution. The pH of the solution was adjusted to 4.8 using 1 M HCl. 0.11 g of delphinidin chloride was then added and stirred in the dark at 27° C. for 2 h. The homogeneous liquid was vacuum-filtered through a cellulose nitrate membrane filter having a pore size of 0.45 µm. The solution was frozen and then freeze-dried at −48° C. and a pressure of about 10.3 Pa (77 mTorr). The lyophilisate was ground and sieved through a sieve of 0.3 mm mesh size.

Example 3.2

Delphinidin/HPBCD

The procedure was the same as for example 3.1, but a significant amount of material was filtered off during the filtration, indicating that the solubilization was distinctly less effective than when using SBE-β-CD in accordance with example 3.1.

Example 3.3

Delphinidin/Starch Formulation g of starch were suspended in 40 ml of distilled water. A white suspension was obtained. The pH of the solution was adjusted to 4.6 using 1 M HCl. 0.11 g of delphinidin chloride was then added and stirred in the dark at 27° C. for 2 h. The homogeneous liquid obtained was freeze-dried, ground and sieved as in example 3.1.

Example 3.1 is in accordance with the invention, and examples 3.2 and 3.3 are comparative examples.

Example 4

Stability Experiments

The solids according to examples 3.1 to 3.3 were stored under the following conditions:
8 days at room temperature in brown, screwed glass containers,
subsequently 22 days at room temperature in glass containers under an oxygen atmosphere in the dark.

The last 22 days of the above-described storage were carried out in glass vials having a volume of 20 ml. 250 mg of each of the samples already stored for 8 days beforehand were filled into said vials, and these were closed and sealed using a rubber stopper. By means of two injection needles, the headspace of the vials was flushed with pure oxygen. The samples were then stored in the dark.

The delphinidin content of the solids (calculated as delphinidin chloride and specified in % by weight) was determined by means of the above-described HPLC method. The results are in table 3 below.

| | Course of time [days] | | | | |
|---|---|---|---|---|---|
| | Start | 2 | 8 | 19 | 30 |
| Example 3.1 | 1.69 | 1.52 | 1.55 | 1.40 | 0.93 |
| Example 3.2 | 1.30 | 1.20 | 1.14 | 1.03 | 0.68 |
| Example 3.3 | 1.60 | 1.59 | 1.56 | 1.53 | 1.15 |

The results show that, according to the invention, it is possible to produce a delphinidin complex which has a high stability and thus a good shelf life even under a pure oxygen atmosphere. The complex further has a good solubility in aqueous solutions, more particularly slightly acidic solutions, making it possible according to the invention to formulate delphinidin in a varied manner. The stability of the solid according to the invention is as good as a formulation containing starch (example 3.3); however, this comparative example cannot be formulated in an aqueous solution.

Example 5

Stability Experiments in Aqueous Solution

The content of delphinidin chloride in the delphinidin-containing solutions was determined by using a reverse-phase HPLC method similar to the one already described above. This used the following reagents:
Purified water
Methanol for chromatography
Formic acid, p. a.
1 M Hydrochloric acid as volumetric solution.

The column used was a Waters X Bridge™ C18, 35 al, 150 mm×4.6 mm.

The mobile phases were as follows:
Channel A: water (770 ml), methanol (230 ml), formic acid (10 ml)
Channel B: water (50 ml), methanol (950 ml), formic acid (10 ml)

The following gradient program was used:

| Time [min] | Percent channel B |
|---|---|
| 0 | 0 |
| 5 | 0 |
| 20 | 20 |
| 25 | 100 |

Stop time: 25 min
Posttime: 8 min
Flow rate: 1 ml/min
Injection volume: 20 µl
Column temperature: 30° C.+/−2° C.
UV/Vis detector: 530 µm for the assay, 275 µm for detecting impurities
Integrator: area
Solutions and Sample Preparation:
Dilution solution 1: mixture of 100 ml of methanol and 2.6 ml of 1 M HCl
Dilution solution 2: mixture of 100 ml of 50% methanol and 2.6 ml of 1 M HCl
Calibration solution: a delphinidin reference solution was produced by weighing out 10 mg of delphinidin chloride into a 10 ml flask and dissolving it in dilution solution 1. After it was dissolved, it was diluted approximately 10-fold using dilution solution 2 to produce an approximate concentration of 0.1 mg/ml.

The control calibration solution was produced in the same manner. The calibration solutions were immediately analyzed by means of HPLC, since delphinidin chloride is unstable in solution.
Production of the Test Solutions:

To determine the delphinidin content of an aqueous solution according to the invention, delphinidin/SBE-β-CD of example 3.1 (according to the invention) and delphinidin (comparative example) were dissolved in 0.9% NaCl solution until a starting concentration (based on the delphinidin) of 1.584 mg/ml (example according to the invention) or 0.0216 mg/ml (comparative example) was set. The solutions were produced at room temperature and then stored in closed vials in the dark at 37° C.

After 1, 2, 3 and 4 h, the delphinidin content was determined. The table below specifies the ascertained content as a percentage of the above-stated starting concentration.

| Time [h] | Delphinidin, uncomplexed | Delphinidin/ SBE-β-CD |
|---|---|---|
| 0 | 100% | 100% |
| 1 | 8.3% | 80.7% |
| 2 | 6.5% | 74.5% |
| 3 | 5.6% | 64.7% |
| 4 | 5.1% | 62.8% |

The determination of the delphinidin content in the samples was calculated with the aid of the Agilent ChemStation software using the calibration with the described external standard.

II. Anti-Inflammatory and Antiphlogistic Effect of Delphinidin and Delphinidin/Sulfoethyl Ether β-Cyclodextrin In Vitro and In Vivo Example 6

In vitro efficacy profile of the prophylactic administration of delphinidin and/or simultaneous administration thereof with lipopolysaccharide (LPS) on cells compared to cells treated only with LPS (control).

Methodology

For healthy test subjects, the concentration of NFKB in the nucleus of monocytes after stimulation with LPS and/or delphinidin was assayed by means of immunofluorescence nuclear staining for NFKB and expressed in relation to nonstimulated cells. NFKB is activated by various stimuli, especially inflammatory and stress-associated stimuli. Inactive NFKB proteins are bound in the cytosol to inhibitor proteins of the IKB family (Baeuerle and Baltimore, 1988, Activation of DNA-binding activity in an apparently cytoplasmic precursor of the NF-kappa B transcription factor, Cell (53), 211-7; Baeuerle and Baltimore, 1988, I kappa B: a specific inhibitor of the NF-kappa B transcription factor, Science (242), 540-6), and the stimulus-dependent proteolytic degradation of various IKB members brings about the nuclear migration of NFKB (Ghosh et al., 1988, NF-kappa B and Rel proteins: evolutionarily conserved mediators of immune responses, Annu Rev Immunol (16), 225-60) and therefore the determination of the extent of the translocation of NFKB from the cytosol into the nucleus is an appropriate detection means for the inflammatory or antiphlogistic effect of compositions to be investigated.

Figure 1:
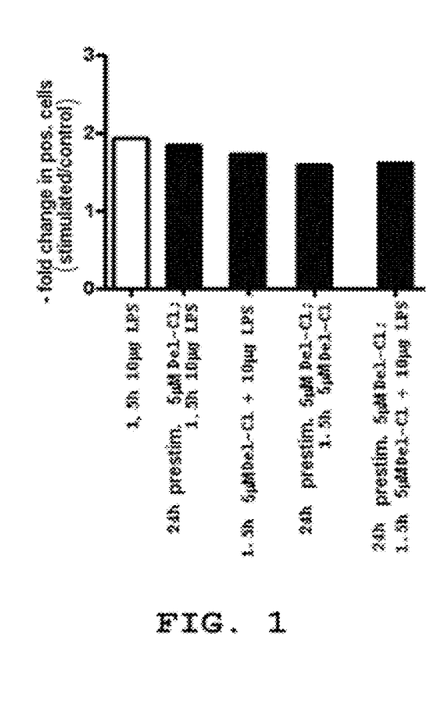
FIG. 1 shows the in vitro efficacy profile of the prophylactic administration of delphinidin and/or simultaneous administration thereof with lipopolysaccharide (LPS) on cells compared to cells treated only with LPS (control).

The following procedure was carried out and shown in FIG. 1 from left to right, with the stimulation/incubation of the cells (1 ml in each case of RPMI-1640 comprising 1 million cells in the exponential growth phase) taking place at 37° C. in a well of a 24-well polystyrene cell culture dish and the specified concentrations being final concentrations:
"1.5 h 10 µg LPS"—Stimulation of the cells for 1.5 h with 10 µg/ml LPS (control)
"24 h prestim. 5 µM Del-Cl; 1.5 h 10 µg LPS"—24 h prestimulation of the cells with 5 µM delphinidin chloride (dissolved in RPMI-1640 cell medium) and then 1.5 h stimulation with 10 µg/ml LPS
"1.5 h 5 µM Del-Cl+10 µg LPS"—1.5 h simulation of the cells with 10 µg/ml LPS and 5 µM delphinidin chloride (dissolved in RPMI-1640 cell medium)
"24 h prestim. 5 µM Del-Cl; 1.5 h 5 µM Del-Cl"—24 h prestimulation of the cells with 5 µM delphinidin chloride (dissolved in RPMI-1640 cell medium) and then renewed stimulation with 5 µM delphinidin chloride (dissolved in RPMI-1640 cell medium) for 1.5 h "24 h prestim. 5 µM Del-Cl; 1.5 h 5 µM Del-Cl+10 µg LPS"—24 h prestimulation of the cells with 5 µM delphinidin chloride (dissolved in RPMI-1640 cell medium) and then renewed stimulation with 5 µM delphinidin chloride (dissolved in RPMI-1640 cell medium) and 10 µg/ml LPS for 1.5 h Results As is apparent from FIG. 1, a prophylactic administration of 5 µM delphinidin for 24 h before the stimulation of the cell immune response with LPS (weakly) inhibits the subsequent 1.5 h LPS-mediated immune response ("24 h prestim. 5 µM Del-Cl; 1.5 h 10 µg LPS" versus "1.5 h 10 µg LPS"); the inhibition of the immune response is less than in the case of simultaneous administration of delphinidin in combination with LPS ("1.5 h 5 µM Del-Cl+10 µg LPS"), and can, by means of prophylactic and repeated addition of 5 µM delphinidin coupled with the addition of LPS ("24 h prestim. 5 µM Del-Cl; 1.5 h 5 µM Del-Cl+10 µg LPS"), be further intensified (additive effect).

Example 7

In vitro efficacy profile of the simultaneous administration of delphinidin or hydrocortisone with lipopolysaccharide (LPS) on cells compared to cells treated only with LPS (control).

Methodology

Figure 2A:
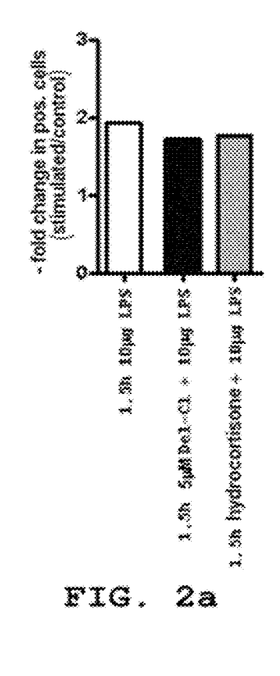
FIG. 2a shows the in vitro efficacy profile of the simultaneous administration of delphinidin or hydrocortisone with lipopolysaccharide (LPS) on cells compared to cells treated only with LPS (control).
Figure 2B:
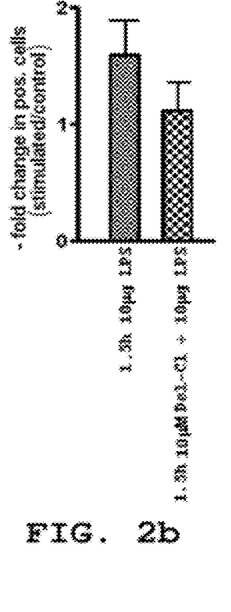
FIG. 2b shows the in vitro efficacy profile of the simultaneous administration of delphinidin with lipopolysaccharide (LPS) on cells compared to cells treated only with LPS (control).

A procedure analogous to the methodology in example 5 was carried out and shown in FIGS. 2a and 2b from left to right, with the stimulation/incubation of the cells (1 ml in each case of RPMI-1640 comprising 1 million cells in the exponential growth phase) taking place at 37° C. in a well of a 24-well polystyrene cell culture dish and the specified concentrations being final concentrations:

FIG. 2a:
"1.5 h 10 µg LPS"—Stimulation of the cells for 1.5 h with 10 µg/ml LPS (control)
"1.5 h 5 µM Del-Cl+10 µg LPS"—1.5 h simulation of the cells with 10 µg/ml LPS and 5 µM delphinidin chloride (dissolved in RPMI-1640 cell medium)
"1.5 h hydrocortisone+10 µg LPS"—Stimulation of the cells for $10^{-5}$ M hydrocortisone and 10 µg/ml LPS for 1.5 h
FIG. 2b:
"1.5 h 10 µg LPS"—Stimulation of the cells for 1.5 h with 10 µg/ml LPS (control)
"1.5 h 10 µM Del-Cl+10 µg LPS"—1.5 h simulation of the cells with 10 µg/ml LPS and 10 µM delphinidin chloride (dissolved in RPMI-1640 cell medium)

Results

As is apparent from FIG. 2a, the LPS-mediated immune response of the cells is, in the case of simultaneous administration of 5 µM delphinidine ("1.5 h 5 µM Del-Cl+10 µg LPS"), inhibited at least just as well as by means of addition of hydrocortisone ("1.5 h hydrocortisone+10 µg LPS") used as comparision. In a repeat experiment shown in FIG. 2b, it was confirmed that the LPS-mediated immune response of the cells is significantly reduced in the case of simultaneous administration of 10 µM delphinidin ("1.5 h 10 µM Del-Cl+10 µg LPS").

Example 8

In vitro efficacy profile of delphinidin on cells when using a varying delphinidin concentration compared to cells treated with hydrocortisone.

Methodology

Figure 3:
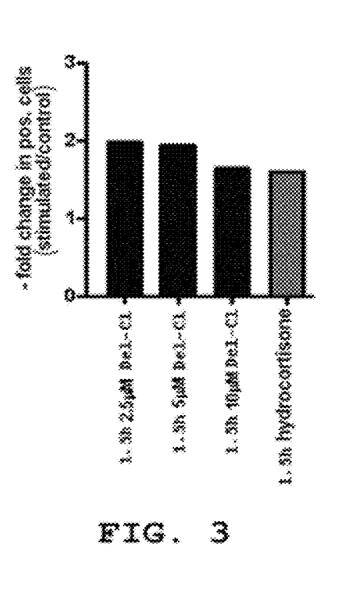
FIG. 3 shows the in vitro efficacy profile of delphinidin on cells when using a varying delphinidin concentration compared to cells treated with hydrocortisone.

A procedure analogous to the methodology in examples 5 and 6 was carried out and shown in FIG. 3 from left to right, with the stimulation/incubation of the cells (1 ml in each case of RPMI-1640 comprising 1 million cells in the exponential growth phase) taking place at 37° C. in a well of a 24-well polystyrene cell culture dish and the specified concentrations being final concentrations:
"1.5 h 2.5 µM Del-Cl"—1.5 h stimulation of the cells with 2.5 µM delphinidin chloride (dissolved in RPMI-1640 cell medium)
"1.5 h 5 µM Del-Cl"—1.5 h simulation of the cells with 5 µM delphinidin chloride (dissolved in RPMI-1640 cell medium)
"1.5 h 10 µM Del-Cl"—1.5 h stimulation of the cells with 10 µM delphinidin chloride (dissolved in RPMI-1640 cell medium)
"1.5 h hydrocortisone"—1.5 h stimulation of the cells with $10^{-5}$ µM hydrocortisone Results As is apparent from FIG. 3, with increasing delphinidin concentration, there is also an increase in the delphinidin-mediated inhibition of the cell immune response (dose effect), with the inhibitory effect at an appropriately high concentration being comparable to that of hydrocortisone.

Example 9

Cell-protective (antiphlogistic/anti-inflammatory) effect of delphinidin on the blood-brain barrier, more particularly influence of delphinidin compared to dexamethasone on the mRNA expression of Cc17 [chemokine (C—C motif) ligand 7] in cEND cells after TNFα [tumor necrosis factor α] treatment or untreated cells in vitro.

Methodology

To investigate the antiphlogistic effect of delphinidin, use was made of an in vitro model of the blood-brain barrier, cEND cells (Forster, C. et al., Occludin as direct target for glucocorticoid-induced improvement of blood-brain barrier properties in a murine in vitro System. J Physiol 565 (Pt 2), 475 (2005)). Said in vitro model consists of the microvascular endothelial cells which were isolated from the murine brain capillaries and immortalized. The cells are seeded on cell culture vessels coated with collagen IV (constituent of the basal lamina around the brain capillaries).

Exposure of cEND cells to tumor necrosis factor alpha (TNFα) and determination of the Cc17 mRNA expression as a marker for inflammation. The reference substance selected for an antiphlogistic effect was dexamethasone, a synthetic steroid hormone having a strong antiphlogistic effect, and the effect of delphinidin in relation to the effect of dexamethasone was plotted in the graph shown in FIG. 4. This was followed by RNA isolation and qPCR analyses of the proinflammatory cytokine, Cc17 (chemokine (C—C motif) ligand 7), also known as Mcp-3 (monocyte chemotactic protein-3).

Figure 4:
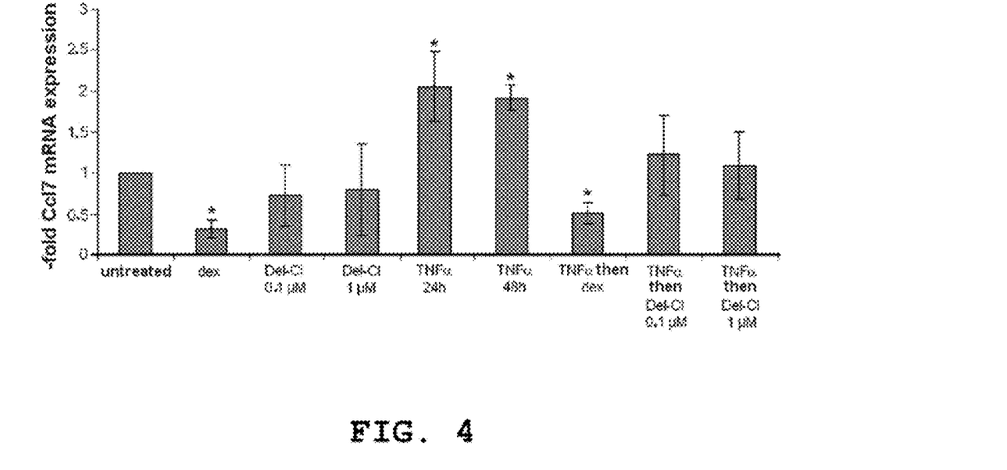
FIG. 4 shows the influence of delphinidin and dexamethasone on the mRNA expression of Cc17 [chemokine (C—C motif) ligand 7] in cEND cells after TNFα [tumor necrosis factor α] treatment or untreated cells in vitro.

The following procedure was carried out and shown in FIG. 4 from left to right:

"untreated"—Control without stimulus
"dex"—Dexamethasone
"Del-Cl 0.1 µM"—Delphinidin (0.1 µmol)
"Del-Cl 1 µM"—Delphinidin (0.1 µmol)
"TNFα 24 h"—Exposure to TNFα for 24 h
"TNFα 48 h"—Exposure to TNFα for 48 h
"TNFα then dex"—Exposure to TNFα for 24 h, then addition of dexamethasone and exposure for a further 24 h
"TNFα then Del-Cl 0.1 µM"—Exposure to TNFα for 24 h, then addition of delphinidin (0.1 µmol) and exposure for a further 24 h
"TNFα then Del-Cl 1 µM"—Exposure to TNFα for 24 h, then addition of delphinidin (1 µmol) and exposure for a further 24 h Results Treatment with TNFα led to the rise in Ccl7 mRNA expression by twofold compared to untreated cells. Addition of delphinidin in the two selected concentrations of 0.1 µM and 1 µM leads to a distinct suppression or inhibition of the TNFα-induced rise in Ccl7 mRNA expression. Interestingly, the addition of delphinidin alone to the cell culture medium without prior TNFα exposure also led to the suppression of Ccl7 expression in the cEND cells. A strong effect was likewise detected in the case of dexamethasone used as comparison.

From the measured results, it can be concluded that the antiphlogistic effect of delphinidin on the blood-brain barrier after inflammation is at least equivalent to the hitherto "gold standard" dexamethasone.

Example 10

(Effect of delphinidin on the barrier properties of the blood-brain barrier, more particularly influence of delphinidin on the mRNA expression of the tight junction protein claudin-5 in cEND cells after TNFα [tumor necrosis factor α] treatment or untreated cells in vitro)

Methodology

The surrogate marker used for the tightness of the barrier was the expression of the tight junction protein claudin-5 (Forster C. Tight junctions and the modulation of barrier function in disease. Histochem Cell Biol. 2008; 130: 55-70) and the procedure carried out was analogous to example 8.

Results

Figure 5:
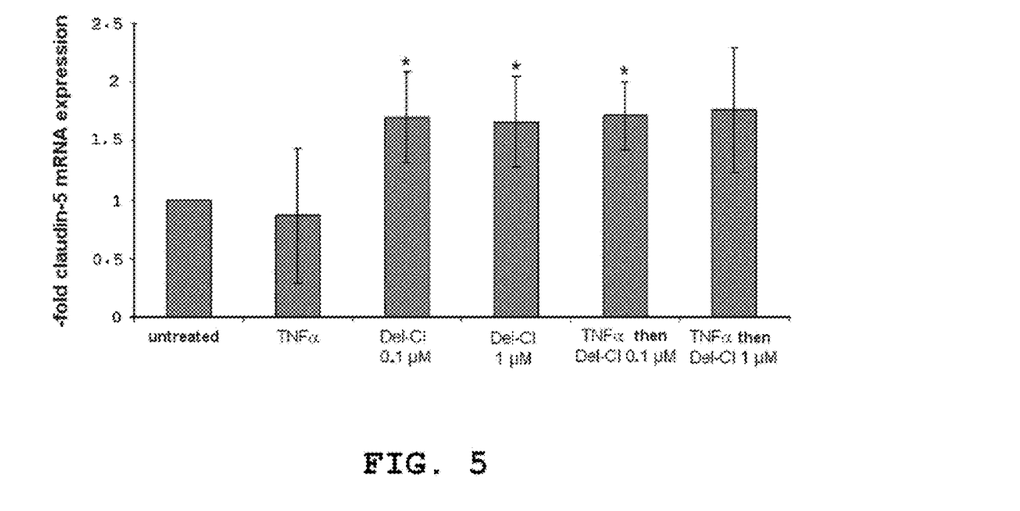
FIG. 5 shows the influence of delphinidin on the mRNA expression of the tight junction protein claudin-5 in cEND cells after TNFα [tumor necrosis factor α] treatment or untreated cells in vitro.

The TNFα treatment led to the decrease in claudin-5 mRNA expression, and the addition of delphinidin after hours counteracted this TNFα-mediated decrease in claudin-5 mRNA expression in the two selected concentrations (0.1 µM and 1 µM), as shown in FIG. 5. Interestingly, the addition of delphinidin alone to the cell culture medium without prior TNFα exposure also led to the increase in claudin-5 mRNA expression.

From the measured results, it can be concluded that the barrier of the blood-brain barrier after inflammation strongly increases under the influence of delphinidin.

Example 11

In vivo influence of delphinidin/sulfoethyl ether β-cyclodextrin on a CFA (complete Freund's adjuvant)-induced inflammation of the rat hind paw.

Methodology a) CFA-induced inflammation of the rat hind paw
CFA is induced intraplantarally at a dose of 150 µl into the right hind paw of a rat under isoflurane anesthesia. The inflammation and the ensuing pain in the inflamed paw develops within 2 to 96 h. Up to this time point, there is no significant difference in the eating pattern, body weight, core temperature or the general activity level compared to the untreated animals (Stein et al., Unilateral inflammation of the hindpaw in rats as a model of prolonged noxious stimulation: alterations in behavior and nociceptive thresholds, Pharmacol Biochem Behav., 1988; 31(2): 445-51).

b) Administration of $H_2O$ (control) and delphinidin/sulfoethyl ether β-cyclodextrin (delphinidin/SEβCD) in different doses
96 hours after aforementioned step a), the rats are injected intraplantarally under isoflurane anesthesia with 100 µl of $H_2O$ (control) or 100 µl of delphinidin/SEPCD at different doses (2.50 mg/ml and 5.00 mg/ml) into the right hind rat paw.

c) Algesiometric measurement method
The rats were habituated to the corresponding experimental conditions as follows:
For the habituation to the Randall-Selitto test, the animals were kept relaxed under a wood pulp 3× per day in the first three days in order to habituate them to the circumstances of the experiment.

The above-mentioned treatment step b) took place on the fourth day, and, starting from time point 0 after the injection, the paw pressure threshold was measured by means of the Randall-Selitto test (instrument from Ugo Basile) after 5, 15, 30, 60, 120 and 240 minutes.

Each paw, ipsilateral and contralateral, is measured three times at an interval of at least 10 s. For the Randall-Selitto test, the rat is kept relaxed under wood pulp and the paw put on a small platform. Then, an increasing pressure is exerted on the paw from above via a stamp until the rat pulls away the paw (Stein et al., Intrinsic mechanisms of antinociception in inflammation: local opioid receptors and beta-endorphin, J Neurosci. 1990; 10(4): 1292-8; Rittner et al., Pain control by CXCR2 ligands through Ca2+-regulated release of opioid peptides from polymorphonuclear cells, FASEB J. 2006; 20(14): 2627-9).

Results

Figure 6:
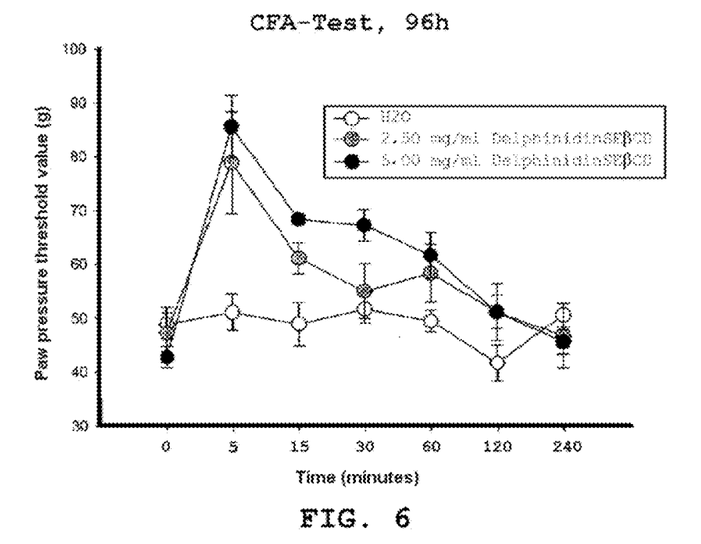
FIG. 6 shows the in vivo influence of intraplantarally administered delphinidin/sulfoethyl ether β-cyclodextrin on a CFA (complete Freund's adjuvant)-induced inflammation of the rat hind paw.

With regard to the FAC-induced inflammatory stimulus in the paw of the rats, the mechanical pain threshold thereof was investigated. From the ascertained paw pressure threshold values shown in graphic form in FIG. 6, it can be deduced that the pain threshold in the case of the administration of delphinidin/SEβCD is significantly reduced with respect to the control injection with $H_2O$, more particularly in the first 120 minutes, with the strongest effect already appearing 5 minutes after the administration of delphinidin/SEβCD. This applies to the two measured doses of 2.5 mg/ml and 5.00 mg/ml delphinidin/SEβCD, it likewise being possible to deduce a dose-dependency from the significantly stronger effect of the higher concentration in the measurement points of the first 30 minutes.

Example 12

Cardioprotection by Means of Delphinidin/Sulfobutyl Ether β-Cyclodextrin (delphinidinSBECD)

Methodology and Results

Figure 7:
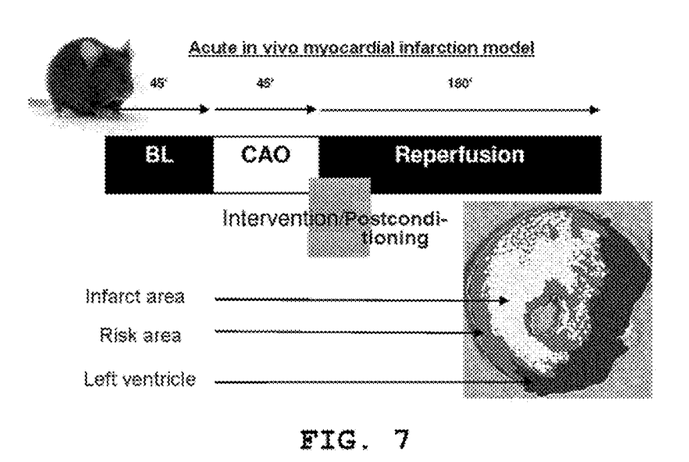
FIG. 7 shows the acute in vivo mouse myocardial infarction model used in example 10 with time course and the affected cardiac regions.
Figure 8:
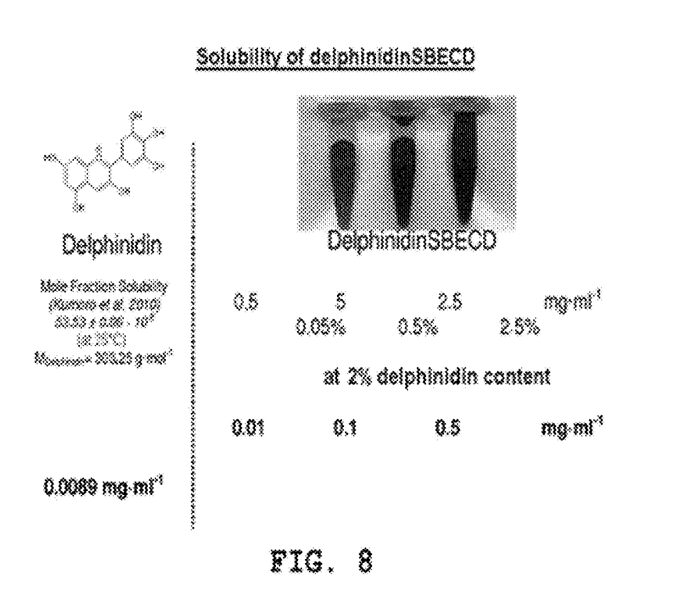
FIG. 8 shows solubilities of delphinidinSBECD.
Figure 9:
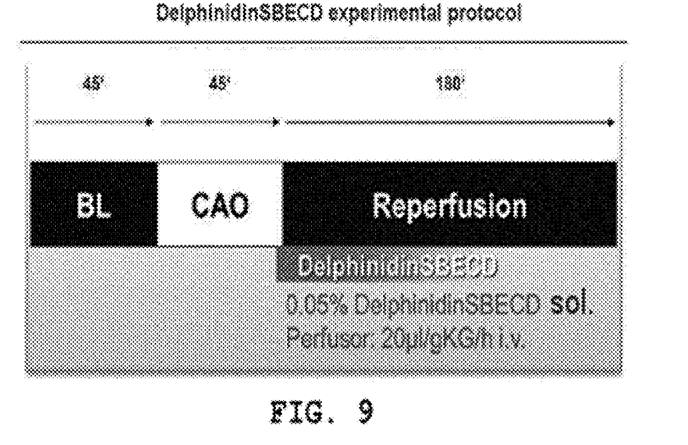
FIG. 9 shows the experimental protocol of use of delphinidinSBECD in the model as per FIG. 7.
Figure 10:
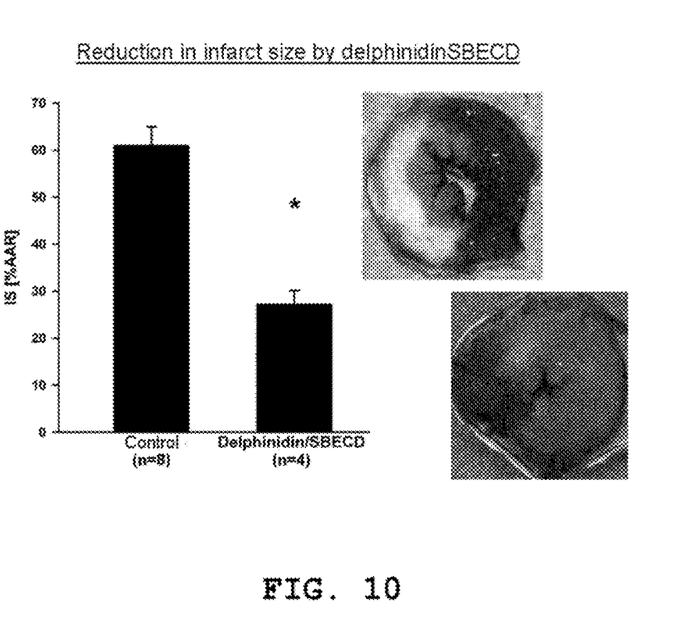
FIG. 10 shows the infarct size as a percentage of the ischemic region for delphinidinSBECD compared to the control group.

In example 11, a possible postconditioning effect of delphinidinSBECD was investigated compared to a control group. To this end, in the in vivo—in situ mouse myocardial infarction model with the time courses shown in FIGS. 7 and 9 using the methodology described in Redel et al., 2008 [Redel et al., Impact of Ischemia and Reperfusion Times on Myocardial Infarct Size in Mice In Vivo. Experimental Biology and Medicine (2008), 233:84-93] and Stumpner et al., 2012 [Stumpner et al., Desflurane-induced post-conditioning against myocardial infarction is mediated by calcium-activated potassium channels: role of the mitochondrial permeability transition pore. British Journal of Anaesthesia (2012), 108(4): 594-601], the resulting infarct size was evaluated and shown graphically in FIG. 10. FIG. 10 specifies mean±SEM; IS=infarct size; AAR=area at risk and *=significantly different from the control group, if p<0.05. The data are shown as mean±standard error of the mean (SEM).

From the ascertained IS and % AAR values shown in graphic form in FIG. 10, it can be deduced that the administration of delphinidinSBECD leads to a significant reduction in infarct size with respect to the control group.

The invention claimed is:

1. A method of anti-inflammatory and/or immunosuppressant treatment, comprising administration of a composition comprising a complex composed of delphinidin and a sulfoalkyl ether β-cyclodextrin to a subject.

2. The method of claim 1, wherein said subject is suffering from or is at risk of cerebral and/or myocardial ischemia.

3. The method of claim 2, wherein a tissue and/or an organ of said subject suffering from or at risk of cerebral and/or myocardial ischemia is at risk of impending reperfusion damage.

4. The method of claim 2, wherein said subject suffering from cerebral ischemia and myocardial ischemia shows clinical symptoms of stroke and of myocardial infarction.

5. The method of claim 1, wherein the sulfoalkyl ether β-cyclodextrin is a sulfobutyl ether β-cyclodextrin or a sulfoethyl ether β-cyclodextrin.

6. The method of claim 1, wherein the degree of substitution of the cyclodextrin with sulfoalkyl ether groups is from 3 to 8.

7. The method of claim 1, wherein the degree of substitution of the cyclodextrin with sulfoalkyl ether groups is from 4 to 8.

8. The method of claim 1, wherein the degree of substitution of the cyclodextrin with sulfoalkyl ether groups is from 5 to 8.

9. The method of claim 1, wherein the degree of substitution of the cyclodextrin with sulfoalkyl ether groups is from 6 to 7.

10. The method of claim 1, wherein the composition comprises a therapeutically effective amount of the complex composed of delphinidin and sulfoalkyl ether β-cyclodextrin.

11. The method of claim 1, wherein the composition is used as a monopreparation.

12. The method of claim 1, wherein the composition comprises at least one further therapeutically active substance.

13. The method of claim 12, wherein the at least one further therapeutically active substance is selected from the group consisting of the groups of anti-inflammatories, of antibodies against inflammatory cytokines, of soluble receptors of inflammatory cytokines, and of immunosuppressants.

14. The method of claim 13, wherein the at least one further therapeutically active substance is selected from the group consisting of acetylsalicylic acid, diclofenac, indomethacin, cyclosporine, azathioprine, bortezomib, melphalan, prednisone, vincristine, carmustine, cyclophosphamide, dexamethasone, thalidomide, doxorubicin, cisplatin, etoposide, and cytarabine.

15. The method of claim 1, wherein the composition further comprises one or more pharmaceutical excipients and/or additives.

16. The method of claim 15, wherein the pharmaceutical excipients and/or additives, are selected from the group consisting of a pharmaceutically acceptable carriers, fillers, odorants, and stabilizers.

17. The method of claim 1, wherein the composition is in a form for administration, said administration selected from the group consisting of oral, rectal, parenteral, including intraperitoneal, percutaneous, subcutaneous, intramuscular, intravenous, ophthalmic, pulmonal, and nasal administration.

18. The method of claim 17, wherein the form for administration is selected from the group consisting of tablet, capsule, suspension, aerosol, solution, cream, paste, lotion, gel, and ointment.

19. The method of claim 1, wherein the complex composed of delphinidin and the sulfoalkyl ether β-cyclodextrin is in a pharmaceutical preparation for the controlled and/or delayed release of the delphinidin.

* * * * *